United States Patent
Purohit et al.

(10) Patent No.: US 6,784,297 B2
(45) Date of Patent: Aug. 31, 2004

(54) PROCESS FOR THE PREPARATION OF ANTI-ISCHEMIC AND ANTI-HYPERTENSIVE DRUG AMLODIPINE BESYLATE

(75) Inventors: Arun Kumar Purohit, Maharashtra (IN); Brahmader Chilu Desai, Maharashtra (IN); Balasaheb Dashrath Shete, Maharashtra (IN); Salim Abbas Bagwan, Maharashtra (IN)

(73) Assignee: Kopran Limited, Mumbai Maharashtra (IN)

( * ) Notice: Subject to any disclaimer, the term of this patent is extended or adjusted under 35 U.S.C. 154(b) by 0 days.

(21) Appl. No.: 10/654,814

(22) Filed: Sep. 4, 2003

(65) Prior Publication Data

US 2004/0044218 A1 Mar. 4, 2004

(30) Foreign Application Priority Data

Sep. 4, 2002 (IN) .................................. 803/MUM/2002

(51) Int. Cl.$^7$ ........................................... C07D 211/90
(52) U.S. Cl. .................................................. 546/321
(58) Field of Search .......................................... 546/321

(56) References Cited

U.S. PATENT DOCUMENTS

| 4,572,909 A | 2/1986 | Campbell et al. |
| 4,879,303 A | 11/1989 | Davison et al. |

FOREIGN PATENT DOCUMENTS

| EP | 0 599 220 A1 | 6/1994 |
| EP | 0 902 016 A1 | 3/1999 |
| EP | 1 125 924 A1 | 8/2001 |
| WO | WO 99/52873 | 10/1999 |
| WO | WO 01/02360 A1 | 1/2001 |

Primary Examiner—Patricia L. Morris
(74) Attorney, Agent, or Firm—Birch, Stewart, Kolasch & Birch, LLP

(57) ABSTRACT

Process for the preparation of anti-ischemic and anti-hypertensive drug amlodipine besylate [2-{(2-aminoethoxy)-methyl-4-(2-chlorophenyl) 3-ethoxy carbonyl-5-methoxycarbonyl-6-methyl-1,4-dihydropyridine} benzene sulphonate]. Phthalic anhydride is condensed with monoethanol amine at 150–190° C. The resulting N-(2-hydroxyethyl) phthalimide is coupled with 4-chloroethyl acetoacetate in the presence of sodium hydride in an organic solvent in an inert atmosphere at −11 to −15° C. Ethyl-4-[-2(phthalimido) ethoxy] acetoacetate formed is coupled with orthochloro benzaldehyde in the presence of pyridine salt at 70–90° C. Ethyl-2-(2-chloro benzylidine)4-[-2(phthalimido) ethoxy] acetoacetate fanned is condensed with methyl amino crotonate at 20–40° C. in the presence of acetic acid to form phthaloyl amlodipine [2-(2-Phthalimidoethoxy) methyl-3-carboethoxy 1(chlorophenyl)-S-carbomethoxy-6-methyl-1,4-dihydropyridin] which is purified by dissolving in an organic solvent in the ratio 1:2–1:5 w/v and precipitated by the addition of water at 35–60° C. Purified phthaloyl amlodipine is hydrolysed with methylamine in the presence of a protic solvent at 20–50° C. Amlodipine base [2-(aminoethoxy) methyl-3-carboethoxy-4-(2-chlorophenyl)-5-carbomethoxy-6-methyl-1,4-dihydropyridin] formed is reacted with benzene sulfonic acid. The resulting amlodipine besylate is purified in an organic solvent at 30–70° C. and precipitated by the addition of an insoluble solvent.

9 Claims, No Drawings

PROCESS FOR THE PREPARATION OF ANTI-ISCHEMIC AND ANTI-HYPERTENSIVE DRUG AMLODIPINE BESYLATE

FIELD OF THE INVENTION

This invention relates to a process for the preparation of anti-ischemic and anti-hypertensive amlodipine besylate.

BACKGROUND OF THE INVENTION

Amlodipine besylate [2-{(2-aminoethoxy)]-methyl-4-(2-chlorophenyl)3-ethoxy carbonyl-5-methoxycarbonyl-6-methyl-1,4-dihydropyridine} benzene sulphonate] is a 1,4-dihydro pyridine based derivative with potent calcium antagonist and vasodilator properties because of which it is an important drug in the treatment of angina and hypertension. It is of the formula I

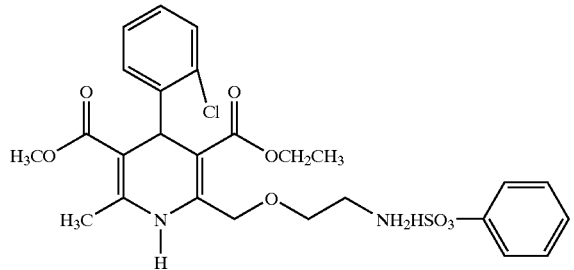

Formula I

Amlodipine {2-[(2-aminoethoxy) methyl]-4-(2-chlorophenyl)-3-ethoxycarbonyl-5-methoxycarbonyl-6-methyl-1,4-dihydropyridine} and its salts were first reported in European Patent No B10089167 which describes preparation of amlodipine and other 1,4-dihydro pyridine compounds from precursors such as phthalimido derivatives without purification. The precursors are corresponding azido derivatives produced by converting amino group by reduction either with Zn/HCl or by hydrogenation over palladium catalyst.

European Patent No B1-0244944 (U.S. Pat. No. 4,879,303) describes preparation of Amlodipine besylate by reacting amlodipine in its free base form with benzene sulfonic acid or ammonium benzene sulfonate an inert solvent such as industrial methanol at 5° C. temperature.

European Patent No 599220 (U.S. Pat. Nos. 5,389,654 and 5,438,145) discloses a process for the preparation of amlodipine benzene sulfonate by reacting trityl-protected amlodipine base with benzene sulfonic acid in a methanolic or an aqueous methanolic medium at 20° C. to reflux temperature. The amlodipine besylate formed is isolated and purified.

European Patent No 0902016 (U.S. Pat. No. 6,046,337) describes a process for the preparation of amlodipine besylate in which benzene sulfonic acid reacts with hexaminium iodide of amlodipine to form amlodipine besylate.

PCT Publication No WO 9952873 (European Patent No 0993447) describes a process for the preparation of amlodipine by reacting an inorganic acid with alkali metal benzene sulfonate in aqueous or alcohol water mixture.

PCT Publication No WO 01/02360 A1 describes a process for the preparation of amlodipine besylate by reacting N carboxy benzoyl derivative of amlodipine base with benzene sulfonic acid.

European Patent No 1125924 discloses a process for the synthesis of amlodipine, where in 3-amino-4-(2-phthalimido)ethoxy) crotonate is used as an intermediate.

Amlodipine besylate generally available contain impurities up to 0.3 to 0.8%. Such level of impurities is not desirable from pharmacological and toxicological considerations.

SUMMARY OF THE INVENTION

An object of this invention is to provide a process for the preparation of anti-ischemic and anti-hypertensive amlodipine besylate which is economical and easy to carry out.

Another object of this invention is to provide a process for the preparation of anti-ischemic and anti-hypertensive amlodipine besylate which is of high purity of the order of 99.9% in good yield.

Another object of this invention is to provide a process for the preparation of anti-ischemic and anti-hypertensive amlodipine besylate which is commercially viable.

DETAILED DESCRIPTION OF THE PREFERRED EMBODIMENT

According to the invention there is provided a process for the preparation of anti-ischemic and anti-hypertensive drug amlodipine besylate 2-{(2-aminoethoxy)-methyl-4 (2-chlorophenyl)3-ethoxy carbonyl-5-methoxycarbonyl-6-methyl-1,4-dihydropyridine} benzene sulphonate] of the formula I

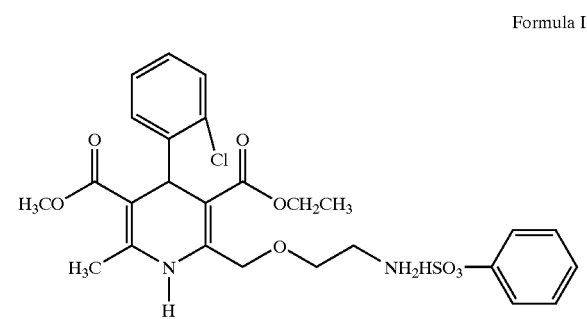

Formula I comprising:

(a) condensation of phthalic anhydride of the formula II

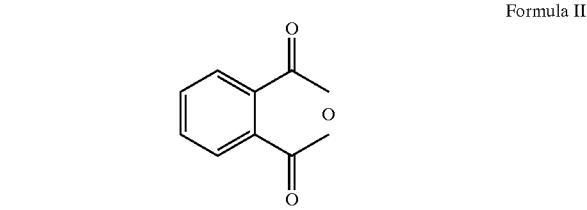

Formula II with monoethanol amine at 150–190° C. to form N-(2-hydroxyethyl)phthalimide of the formula III

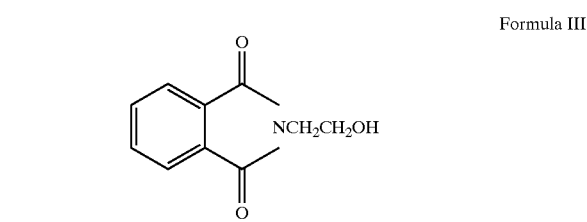

Formula III (b) coupling the compound of the formula III with 4-chloroethyl acetoacetate in the presence of sodium hydride in an organic solvent in an inert atmosphere at −11 to −15° C. to form ethyl-4-[-2(phthalimido) ethoxy] acetoacetate of the formula IV Formula IV

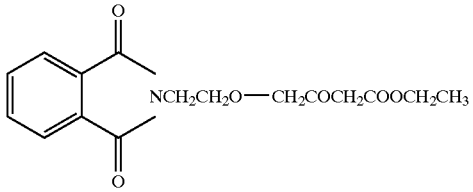

(c) coupling the compound of the formula IV with orthochloro benzaldehyde in the presence of pyridine salt at 70–90° C. to form ethyl-2-(2-chloro benzylidine) 4-[-2(phthalimido)ethoxy] acetoacetate of the formula V Formula V

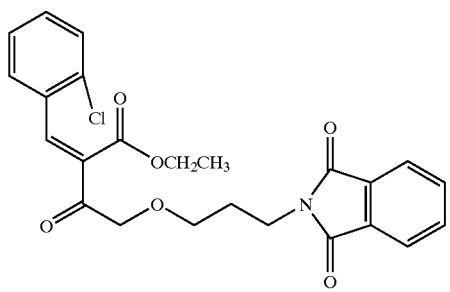

(d) condensing the compound of the formula V with methyl amino crotonate at 20–40° C. in the presence of acetic acid to form phthaloyl amlodipine [2-(2-Phthalimidoethoxy) methyl-3-carboethoxy 1(chlorophenyl)-5-carbomethoxy-6-methyl-1,4-dihydropyridin] of the formula VI Formula VI

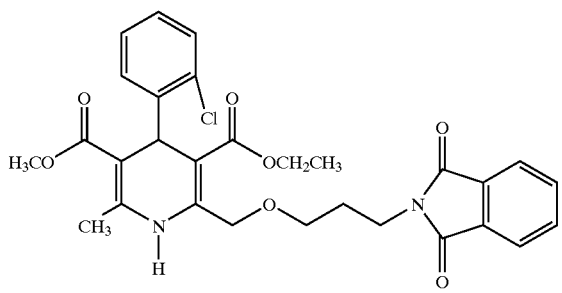

(e) purifying the compound of the formula VI by dissolving it in an organic solvent in the ratio 1:2–1:5 w/v followed by precipitation by the addition of water at 35–60° C.;

(f) hydrolysing the purified compound of the formula VI with methylamine in the presence of a protic solvent at 20–50° C. to form amlodipine base [2-(aminoethoxy) methyl-3-carboethoxy-4-(2-chlorophenyl)-5-carbomethoxy-6-methyl-1,4-dihydropyridin] of the formula VII Formula VII

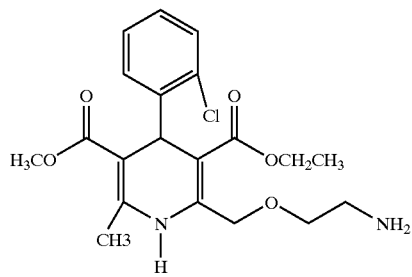

(g) reacting the amlodipine base of the formula VII with benzene sulfonic acid to form the amlodipine besylate; and (h) purifying the amlodipine besylate by dissolving it in an organic solvent at 30–70° C. and precipitating it by the addition of an insoluble solvent.

According to the invention there is provided a process for the preparation of amlodipine besylate which employs inexpensive solvents and reagents and is, therefore, economical.

The reaction conditions of the invention are simple to follow. Therefore, it is easy to carry out. Besides, amlodipine besylate is obtained in very high purity of the order of 99.9% by the steps of purification of the intermediate phthaloyl amlodipine followed by hydrolysis in protic solvent and purification of the amlodipine besylate. For the above reasons, the process of the invention is commercially viable.

Purification of phthaloyl amlodipine is preferably carried out by dissolving it in an organic solvent in the ratio of 1.2 to 1.5 w/v at 40–60° C. The organic solvent used for purification of phthaloyl amlodipine may be selected from acetone, methanol, denatured spirit, isopropyl alcohol, 1,4 dioxane or dimethyl formamide, preferably acetone.

Hydrolysis of phthaloyl amlodipine to amlodipine is carried out with a protic solvent such as ethanol, denatured spirit, methanol, isopropyl alcohol, chloroform or dioxane, preferably denatured spirit. The hydrolysis may be preferably carried out at room temperature.

Purification of amlodipine besylate is carried out in an organic solvent such as methanol, ethanol or chloroform, preferably methanol or chloroform. Purification of amlodipine besylate is carried out preferably at 65° C.

Precipitation of amlodipine besylate is carried out using an insoluble solvent (i.e. a solvent in which amlodipine is insoluble) such as water, isopropyl alcohol or butanol, preferably isopropyl alcohol.

The following examples are illustrative of the invention but not limitative of the scope thereof.

EXAMPLE 1

Preparation of N-(2-Hydroxyethyl)phthalimide

Phthalic anhydride (100 g, 0.67M) was condensed with monoethanol amine (41.2 g, 0.91 M) at 160–178° C. for 4 hours. The reaction mass was quenched in hot water at 95° C., cooled and filtered and washed with water twice and dried at 90–95° C. for 12 hours. Yield 118 g.

Preparation of Ethyl 4[2-(Phthalimido)ethoxy] Acetoacetate

N-(2-hydroxyethyl) phthalimide (100 g, 0.52 M) was coupled with 4-chloroethyl acetoacetate (50 g, 0.30 M) in the presence of sodium hydride in toluene under nitrogen atmosphere at −11 to −15° C. and at 25–30° C. for 12 hours and at 45° C. for 1 hour. The reaction mass was quenched in acidic water and extracted with toluene. The toluene extract was subjected to distillation and residue was degassed below 60° C.

Preparation of Ethyl-2-(2-chlorobenzylidine)-4-[2(phthalimido)ethoxy] Acetoacetate Orthochlorobenzaldehyde (67.5 g, 0.48 M) was reacted with ethyl 4[2-(phthalimido)ethoxy acetoacetate (100 g, 0.31 M) in the presence of pyridine acetic acid in benzene at 80/82° C. for 12 hrs and cooled to room temperature. To the reaction mass water was added. Organic layer was separated and benzene was distilled out and the residue was washed with hexane.

Preparation of Phthaloyl Amlodipine

Ethyl-2-(2-chlorobenzylidine)-4-[2(Phthalimido)ethoxy] acetoacetate residue was condensed with 3-methyl aminocrotonate (153 g, 1.33 M) in acetic acid for 16 hours, filtered, washed twice with acetic acid and n-hexane and dried at 60–70° C. for 8 hours. Yield=140 g. Purity: 97.5%.

Purification of Phthaloyl Amlodipine

Phthaloyl amlodipine (100 g, 0.18 M) was dissolved in 350 ml of acetone at 45° C. and 100 ml of water was slowly added to precipitate the product which was cooled and dried for 12 hrs at 50° C. Yield=95.5 g, Purity: 99.3%.

Preparation of Amlodipine Base

Phthaloyl amlodipine (100 g, 0.18 M) was reacted with monomethyl amine (500 g, 40% solution) in denatured spirit at room temperature for 8 hrs, cooled to 0° C., filtered, washed with distilled water up to neutral pH and dried at 60–65° C. for 8 ills. Yield 58 g.

Amlodipine Base to Amlodipine Besylate

Amlodipine base (100 g, 0.24 M) was reacted with benzene sulphonic acid (59 g, 0.37M) in aqueous medium for 3 hrs, filtered and washed with water till pH was 4.0. The wet reaction mass was treated with activated charcoal in methanol at 50° C., distilled, degassed and crystallized in ethyl acetate, washed with ethyl acetate and acetone (chilled) and dried at 60–65° C. Yield=120 g. Purity: 99.5%.

Purification of Amlodipine Besylate

Amlodipine besylate (100 g, 0.17M) was dissolved in methanol at 65° C. and precipitated by the addition of isopropyl alcohol, cooled and chilled to 10° C., filtered, washed with chilled isopropyl alcohol and dried at 60–65° C. for 8 hrs. Yield=92 gm. Purity=99.9%.

EXAMPLE 2

The procedure of Example 1 was followed except that in the purification of phthaloyl amlodipine 500 ml of acetone and 140 ml of water were used. Yield: 94 g. Purity: 99.85%.

EXAMPLE 3

The procedure of Example 1 was followed except that in the purification of phthaloyl amlodipine 250 ml of acetone and 90 ml of water were used. Yield: 93 g. Purity: 99.9%.

EXAMPLE 4

The procedure of Example 1 was followed except that in the purification of phthaloyl amlodipine 500 ml of acetone and 150 ml of water were used. Yield: 92 g. Purity: 99.88%.

EXAMPLE 5

The procedure of Example 1 was followed except that in the preparation of amlodipine base phthaloyl amlodipine was hydrolysed with monomethylamine in methanol.
Yield: 91.5 g. Purity: 99.9%.

EXAMPLE 6

The procedure of Example I was followed except that purification of amlodipine besylate was carried out by dissolution in chloroform at 50° C. followed by precipitation with isopropyl alcohol. Yield: 91 g. Purity: 99.86%.

EXAMPLE 7

The procedure of Example I was followed without purification of phthaloyl amlodipine and amlodipine besylate. Yield: 120 g. Purity: 98.5%.

What is claimed is:

1. A process for the preparation of anti-ischemic and anti-hypertensive drug amlodipine besylate [2-{(2-aminoethoxy)-methyl-4-(2-chlorophenyl)3-ethoxy carbonyl-5-methoxycarbonyl-6-methyl-1,4-dihydropyridine} benzene sulphonate] of a formula I Formula I

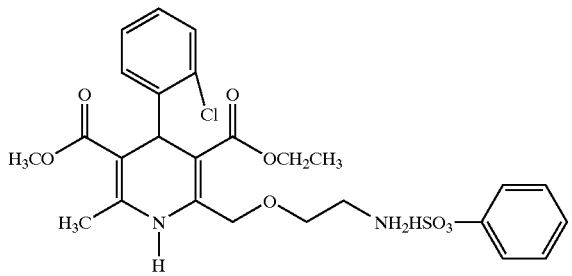

comprising:

(a) condensating phthalic anhydride of a formula II

Formula II

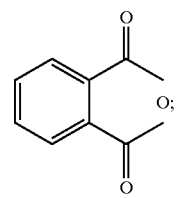

with monoethanol amine at a temperature of between about 150° C. and about 190° C. to form N-(2-hydroxyethyl)phthalimide of a formula III Formula III

(b) coupling the compound of the formula III with 4-chloroethyl acetoacetate in the presence of sodium hydride in an organic solvent in an inert atmosphere at a temperature of about −11° C. to about −15° C. to form ethyl-4-[-2(phthalimido) ethoxy] acetoacetate of a formula IV Formula IV

[Structure: 2-acetylbenzoyl group attached to NCH₂CH₂O—CH₂COCH₂COOCH₂CH₃]

(c) coupling the compound of the formula IV with orthochloro benzaldehyde in the presence of pyridine salt at a temperature of about 70° C. to about 90° C. to form ethyl-2-(2-chloro benzylidine) 4-[-2(phthalimido) ethoxy] acetoacetate of a formula V Formula V

[Structure of Formula V]

(d) condensing the compound of the formula V with methyl amino crotonate at a temperature of about 20 to about 40° C. in the presence of acetic acid to form phthaloyl amlodipine [2-(2Phthalimidoethoxy)methyl-3-carboethoxy 1(chlorophenyl)-5-carbomethoxy-6-methyl-1,4-dihydropyridin] of a formula VI Formula VI

[Structure of Formula VI]

(e) purifying the compound of the formula VI by dissolving it in an organic solvent in a ratio of about 1:2 and about 1:5 w/v followed by precipitation by the addition of water at a temperature between about 35° C. and about 60° C.;

(f) hydrolyzing the purified compound of the formula VI with methylamine in the presence of a protic solvent at a temperature of about 20° C. to about 50° C. to form amlodipine base [2-(aminoethoxy) methyl-3-carboethoxy-4-(2-chlorophenyl)-5-carbomethoxy-6-methyl-1,4-dihydropyridin] of a formula VII Formula VII

[Structure of Formula VII - amlodipine base]

(g) reacting the amlodipine base of the formula VII with benzene sulfonic acid to form amlodipine besylate;

(h) purifying amlodipine besylate by dissolving it in an organic solvent at a temperature of about 30° C. and about 70° C. and precipitating it by addition of an insoluble solvent.

2. The process of claim 1, wherein said purifying of phthaloyl amlodipine is carried out by dissolving it in an organic solvent in a ratio of between about 1:2 and about 1:5 w/v.

3. The process of claim 1, wherein purifying of phthaloyl amlodipine is carried out by dissolving it in organic solvent at a temperature of between about 40 and about 60° C.

4. The process of claim 1, wherein purifying of phthaloyl amlodipine is carried out by dissolving it in acetone.

5. The process of claim 1, wherein hydrolyzing of purified phthaloyl amlodipine is carried out in the presence of denatured spirit.

6. The process of claim 1, wherein the hydrolyzing of purified phthaloyl amlodipine of the formula VI is carried out at room temperature.

7. The process of claim 1, wherein said purifying of amlodipine besylate is carried out in methanol or chloroform.

8. The process of claim 1, wherein said purifying of amlodipine besylate is carried out at 65° C.

9. The process of claim 1, wherein said precipitating of amlodipine besylate is carried out with isopropyl alcohol.

* * * * *